United States Patent
Sutton et al.

(10) Patent No.: US 11,306,039 B1
(45) Date of Patent: Apr. 19, 2022

(54) SYSTEM AND METHOD FOR MAKING FUELS

(71) Applicant: Triad National Security, LLC, Los Alamos, NM (US)

(72) Inventors: Andrew D. Sutton, White Rock, NM (US); Cameron M. Moore, White Rock, NM (US); Orion Staples, Philadelphia, PA (US); Troy A. Semelsberger, Los Alamos, NM (US); William L. Kubic, Jr., White Rock, NM (US)

(73) Assignee: Triad National Security, LLC, Los Alamos, NM (US)

( * ) Notice: Subject to any disclaimer, the term of this patent is extended or adjusted under 35 U.S.C. 154(b) by 131 days.

(21) Appl. No.: 16/431,372

(22) Filed: Jun. 4, 2019

Related U.S. Application Data (60) Provisional application No. 62/680,900, filed on Jun. 5, 2018.

(51) Int. Cl.

| | |
|---|---|
| *C07C 1/24* | (2006.01) |
| *C10L 1/02* | (2006.01) |
| *C07C 45/59* | (2006.01) |
| *C07C 29/10* | (2006.01) |
| *B01J 19/24* | (2006.01) |
| *B01J 19/00* | (2006.01) |
| *B01J 23/72* | (2006.01) |
| *B01J 21/04* | (2006.01) |
| *B01J 23/755* | (2006.01) |

(Continued)

(52) U.S. Cl.
CPC ............... *C07C 1/24* (2013.01); *B01D 3/143* (2013.01); *B01J 19/0013* (2013.01); *B01J 19/245* (2013.01); *B01J 21/04* (2013.01); *B01J 21/12* (2013.01); *B01J 23/72* (2013.01); *B01J 23/755* (2013.01); *C07C 2/08* (2013.01); *C07C 29/103* (2013.01); *C07C 45/59* (2013.01); *C10L 1/02* (2013.01); *B01J 2219/00033* (2013.01); *B01J 2219/00157* (2013.01); *C07C 2601/08* (2017.05); *C07C 2601/10* (2017.05)

(58) Field of Classification Search
CPC .. C07C 1/24; C07C 45/59; C07C 2/08; C07C 29/103; C07C 2601/10; C07C 2601/08; B01J 23/755; B01J 19/0013; B01J 23/72; B01J 21/12; B01J 19/245; B01J 21/04; B01J 2219/00157; B01J 2219/00033; C10L 1/02; B01D 3/143
See application file for complete search history.

(56) References Cited

U.S. PATENT DOCUMENTS

| | | |
|---|---|---|
| 2,623,072 A | 12/1952 | Ray |
| 4,270,014 A | 5/1981 | Norton et al. |

OTHER PUBLICATIONS

Wang et al. ,"Recent Advances in Catalytic Hydrogenation of Furfural"; Catalysts 2019, 9, 796; Accepted: Sep. 19, 2019; Published: Sep. 24, 2019 (Year: 2019).*

(Continued)

*Primary Examiner* — Ali Z Fadhel
(74) *Attorney, Agent, or Firm* — Klarquist Sparkman, LLP (57) ABSTRACT

Embodiments of a system and method are disclosed for obtaining high-energy fuels. In some embodiments, the system and method produces one or more fused cyclic compounds that can include one or more bridging points. The fused cyclic compounds are suitable for use as a high-energy fuels, and may be derived from biomass.

11 Claims, 4 Drawing Sheets

(51) Int. Cl.
  *B01J 21/12*   (2006.01)
  *B01D 3/14*    (2006.01)
  *C07C 2/08*    (2006.01)

(56) References Cited

OTHER PUBLICATIONS

Yan et al., "Production, properties and catalytic hydrogenation of furfural to fuel additives and value-added chemicals", Renewable and Sustainable Energy Reviews 38 (2014) 663-676. (Year: 2014).*
Aria et al., "Production of 2-methylfuran from biomass through an integrated biorefinery approach", Fuel Processing Technology 178 (2018) 336-343; Available online Jun. 7, 2018. (Year: 2018).*
Hronec et al., "Selective transformation of furfural to cyclopentanone," *Catalysis Communications,* 24(5): 100-104, Jul. 5, 2012.
King, "Very low-pressure pyrolysis (VLPP) of cyclopentene," *International Journal of Chemical Kinetics,* 10(1): 117-123, Jan. 1978.
Knecht et al., "Thermal decomposition of cyclopentene and cyclopentene-$d_8$ in the gas phase," *J. Am. Chem. Soc.,* 95(24): 7933-7928, Nov. 28, 1973.
Lewis et al., "Stereochemistry of molecular hydrogen elimination from cyclopentene at 1100-1300 K," *J. Phys. Chem.,* 85(13): 1783-1786, Jun. 1, 1981.
Ma et al., "Selective conversion of furfural to cyclopentanol over cobalt catalysts in one step," *Chinese Chemical Letters,* vol. 28, pp. 1153-1158, Mar. 12, 2017.
Maki et al., "Chemoselective hydrogenation of carbonyl compounds over heterogeneous catalysts," *Applied Catalysis A: General,* vol. 292, pp. 1-49, Aug. 1, 2005.
Mittal et al., "Production of Furfural from Process-Relevant Biomass-Derived Pentoses in a Biphasic Reaction System," *ACS Sustainable Chemistry & Engineering,* 5(7): 5694-5701, May 16, 2017.
Sibi et al., "Single-step catalytic liquid-phase hydroconversion of DCPD into high energy density fuel exo-THDCPD," *Green Chem.,* 14(4): 976-983, Feb. 13, 2012.
Wongsawa et al., "Solubility and tie-line data for ternary aqueous mixtures of cyclopentanol with organic solvents at T=298.2 K: experiments and NRTL model," *Fluid Phase Equilibria,* 379(15): 10-18, Oct. 15, 2014.
Yakabe et al., "Practical reduction of carbonyl compounds with $NaBH_4$ and silica gel in an aprotic solvent," *Synthetic Communications,* 29(2): 295-302, 1999.
Zhang et al., "Towards quantitative and scalable transformation of furfural to cyclopentanone with supported gold catalysts," *Green Chemistry,* 18(7): 2155-2135, Nov. 26, 2015.
Harries et al., "Conversion of cyclopentene into the mono-and di-aldehydes of glutaric acid," *Chem. Ber.,* vol. 41, 1908.

* cited by examiner

SYSTEM AND METHOD FOR MAKING FUELS

CROSS REFERENCE TO RELATED APPLICATIONS

This application claims the benefit of the earlier filing date of U.S. Provisional Application No. 62/680,900, filed Jun. 5, 2018, which is incorporated herein by reference in its entirety.

ACKNOWLEDGMENT OF GOVERNMENT SUPPORT

This invention was made with government support under Contract No. 89233218CNA000001 awarded by the U.S. Department of Energy/National Nuclear Security Administration. The government has certain rights in the invention.

FIELD

The present disclosure concerns embodiments of a system and a method for making fuels from readily available sources.

BACKGROUND

Sustainable methods of making transportation fuels, such as aviation fuels having bridged hydrocarbons, from renewable resources is becoming increasingly important. Methods used to date to obtain aviation fuels involve complex synthetic methodologies that require elevated temperatures and harsh reaction conditions. Additionally, strong Lewis acids that are employed in such methods result in undesirable by-products that can significantly reduce the overall yields of the fuels, thereby limiting the economic viabilities of such methods in their industrial applications.

There exists a need in the art for a reliable, cost-efficient, scalable method for the producing transportation fuels from readily available starting materials and systems for carrying out such methods.

SUMMARY

Disclosed herein are embodiments of a system and a method for preparing high-energy fuels. In some embodiments, the system comprises a combination of reactors, columns, and other components that facilitate preparing high energy fuels from readily-available sources, such as biomass. System embodiments and components included therein are described herein. Also disclosed are process embodiments for preparing the high energy fuels from sources like biomass. Reagents, starting materials, and intermediates of such process embodiments are described herein.

The foregoing and other objects and features of the present disclosure will become more apparent from the following detailed description, which proceeds with reference to the accompanying figures.

DETAILED DESCRIPTION

I. Explanation of Terms

The following explanations of terms are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting, unless otherwise indicated. Other features of the disclosure are apparent from the following detailed description and the claims.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that can depend on the desired properties sought and/or limits of detection under standard test conditions/methods. When directly and explicitly distinguishing embodiments from discussed prior art, the embodiment numbers are not approximates unless the word "about" is recited. Furthermore, not all alternatives recited herein are equivalents.

Also, the following description is exemplary in nature and is not intended to limit the scope, applicability, or configuration of the present disclosure. Various changes to the described embodiment may be made in the function and arrangement of the elements described herein without departing from the scope of the preset disclosure. Further, descriptions and disclosures provided in association with one particular embodiment are not limited to that embodiment, and may be applied to any embodiment disclosed. Further, the terms "coupled" and "associated" generally mean fluidly, electrically, and/or physically (e.g., mechanically or chemically) coupled or linked and does not exclude the presence of intermediate elements between the coupled or associated items absent specific contrary language.

Although the operations of exemplary embodiments of the disclosed method and/or system embodiments may be described in a particular, sequential order for convenient presentation, it should be understood that disclosed embodiments can encompass an order of operations other than the particular, sequential order disclosed, unless the context dictates otherwise. For example, operations described sequentially may in some cases be rearranged or performed concurrently. Further, descriptions and disclosures provided in association with one particular embodiment are not limited to that embodiment, and may be applied to any disclosed embodiment.

To facilitate review of the various embodiments of the disclosure, the following explanations of specific terms are provided.

Aliphatic: A hydrocarbon, or a radical thereof, having at least one carbon atom (or two or three or four or five or more carbon atoms) to 50 carbon atoms, such as one carbon atom (or two or three or four or five or more carbon atoms) to 25 carbon atoms, or one carbon atom (or two or three or four or five or more carbon atoms) to ten carbon atoms, and which includes alkanes (or alkyl), alkenes (or alkenyl), alkynes (or alkynyl), including cyclic versions thereof, and further including straight- and branched-chain arrangements, and all stereo and position isomers as well. Aliphatic groups are distinct from aromatic groups.

Alkyl: A saturated monovalent hydrocarbon having at least one carbon atom (or two or three or four or five or more carbon atoms) to 50 carbon atoms, such as one carbon atom (or two or three or four or five or more carbon atoms) to 25 carbon atoms, or one carbon atom (or two or three or four or five or more carbon atoms) to ten carbon atoms, wherein the saturated monovalent hydrocarbon can be derived from removing one hydrogen atom from one carbon atom of a parent compound (e.g., alkane). An alkyl group can be branched, straight-chain, or cyclic (e.g., cycloalkyl).

Alkenyl: An unsaturated monovalent hydrocarbon having at least two carbon atoms (or three or four or five or six or more carbon atoms) to 50 carbon atoms, such as two carbon atoms (or three or four or five or six or more carbon atoms) to 25 carbon atoms, or two carbon atoms (or three or four or five or six or more carbon atoms) to ten carbon atoms, and at least one carbon-carbon double bond, wherein the unsaturated monovalent hydrocarbon can be derived from removing one hydrogen atom from one carbon atom of a parent alkene. An alkenyl group can be branched, straight-chain, cyclic (e.g., cycloalkenyl), cis, or trans (e.g., E or Z).

Alkynyl: An unsaturated monovalent hydrocarbon having at least two carbon atoms (or three or four or five or six or more carbon atoms) to 50 carbon atoms, such as two carbon atoms (or three or four or five or six or more carbon atoms) to 25 carbon atoms, or two carbon atoms (or three or four or five or six or more carbon atoms) to ten carbon atoms and at least one carbon-carbon triple bond, wherein the unsaturated monovalent hydrocarbon can be derived from removing one hydrogen atom from one carbon atom of a parent alkyne. An alkynyl group can be branched, straight-chain, or cyclic (e.g., cycloalkynyl).

Aromatic: A cyclic, conjugated group or moiety of, unless specified otherwise, from 5 to 15 ring atoms having a single ring (e.g., phenyl) or multiple condensed rings in which at least one ring is aromatic (e.g., naphthyl, indolyl, or pyrazolopyridinyl); that is, at least one ring, and optionally multiple condensed rings, have a continuous, delocalized π-electron system. Typically, the number of out of plane π-electrons corresponds to the Hückel rule (4n+2). The point of attachment to the parent structure typically is through an aromatic portion of the condensed ring system. For example However, in certain examples, context or express disclosure may indicate that the point of attachment is through a non-aromatic portion of the condensed ring system. For example, An aromatic group or moiety may comprise only carbon atoms in the ring, such as in an aryl group or moiety, or it may comprise one or more ring carbon atoms and one or more ring heteroatoms comprising a lone pair of electrons (e.g. S, O, N, P, or Si), such as in a heteroaryl group or moiety. Aromatic groups may be substituted with one or more groups other than hydrogen, such as aliphatic, heteroaliphatic, haloaliphatic, haloheteroaliphatic, aromatic, or an organic functional group.

Aryl: An aromatic carbocyclic group comprising at least five carbon atoms to 15 carbon atoms, such as five to ten carbon atoms, having a single ring or multiple condensed rings, which condensed rings can or may not be aromatic provided that the point of attachment is through an atom of the aromatic carbocyclic group.

Biomass: An organic material that is used to produce energy, such as in the form of energetic fuels. In some embodiments, the biomass refers to any hemicellulosic or lignocellulosic material that comprises cellulose, lignin, starch, oligosaccharides, and/or monosaccharides.

Bridged compound: A chemical compound that has two or more rings bonded together in a manner that provides a bridge containing at least one atom between the rings, wherein the bridging atom (or atoms) connects two or more bridgehead atoms. Exemplary bridged compounds may include, but are not limited to, Carbonyl: —C(O)—.

Dehydrating Agent: A compound, or mixture of compounds, capable of converting an alcohol-containing compound to an alkene-containing compound by promoting a loss of $H_2O$ from the alcohol-containing compound.

Octane number: A measure of the performance of an engine or aviation fuel. A person of ordinary skill in the art with the benefit of the present disclosure will understand that the higher octane number, the more compression the fuel can withstand before igniting.

A person of ordinary skill in the art would recognize that the definitions provided above are not intended to include impermissible substitution patterns (e.g., methyl substituted with 5 different groups, and the like). Such impermissible substitution patterns are easily recognized by a person of ordinary skill in the art. In some embodiments, dehydrogenation catalyst structures and/or formulas are provided herein that can have an overall complex charge that is neutralized with a suitable counterion. Any functional group disclosed herein and/or defined above can be substituted or unsubstituted, unless otherwise indicated herein.

II. Introduction

Transportation fuels (also referred to herein as "high-energy fuels"), such as aviation fuels comprising hydrocarbon compounds, can possess a combination of properties that are suitable for use with space propulsion systems and other flight systems, such as jet propulsion or rocket propulsion, where operational temperatures (for example, temperatures from 1000 to 2500 K) and pressures (for example, from 0.1 to 10 MPa) are often high. These combinations of properties which, for example, may be substantially improved as compared to the properties of conventional petroleum-based fuels (such as JP-8), may include, but are not limited to, appreciably high density (for example, 0.94 $g/cm^3$ or higher), high boiling point (for example, 187° C. or higher), low freezing point (for example, −79° C.), high heat of combustion (for example, 39.4 MJ/L or higher) and a high volumetric energy density. However, using such high-energy fuels is currently limited, in part, due to cost (which, for example, is roughly $25/gallon) and low production volume constraints.

Current synthetic methods for producing high-energy fuels can use pyrolysis gasoline as a primary feedstock. Pyrolysis gasoline, a naphtha-range product with high aromatics content, is a by-product in producing ethylene via steam cracking from a variety of feeds, such as ethane, propane, butane, naphtha, atmospheric gas oils, liquid petroleum gas (LPG), crude oil and/or vacuum gas oils. A component of pyrolysis gasoline (also commonly referred to as "pygas") is cyclopentadiene, which can be obtained in approximately 0.14% by mass, when producing ethylene. Cyclopentadiene can subsequently be subjected to one or more reactions, such as dimerization, dehydrogenation and isomerization, to produce the desired high-energy fuel, such as JP-10.

While naphtha has been a preferred starting material in steam cracking for producing ethylene, it has been replaced by ethane obtained from shale gas, partly due to its affordability and increased abundance. However, current methods that involve cracking ethane from shale gas are so efficient that fewer by-products, including the much-needed pyrolysis gasoline, are produced, thus dramatically limiting the availability of high-energy fuel precursors. Alternative synthetic methods, preferably those that can use readily available feedstocks, that can significantly reduce the cost and production constraints are needed to significantly expand the market size of these high-energy fuels. The present disclosure addresses these issues. For instance, improved and sustainable system and method embodiments are disclosed that produce high-energy fuels, which can be used as jet and/or rocket fuels, and also can be used in gas turbines for trains, naval and civilian marine, and/or energy storage applications.

III. Method of Making High-Energy Fuel

Disclosed herein are embodiments of a method for making high-energy fuels from readily available feedstocks, such as biomass. Embodiments of the disclosed method are highly selective, high-yielding and chemo-catalytic. Method embodiments disclosed herein can operate at relatively low temperatures and pressures, resulting in a high-energy fuel that can be obtained in a cost effective manner that is scalable and reproducible. The disclosed method embodiments also can be used to make high-energy fuels that can also be used as a future fuel for advanced combustion engines.

In certain disclosed embodiments, 5-membered or 6-membered sugars and/or carbohydrates derived from biomass can be utilized in a tandem approach to produce substituted cycloalkanes (such as, substituted cyclopentanes), which can then be defunctionalized and dimerized to a cyclic diene (such as, cyclopentadiene dimer). The cyclic diene can serve as a precursor in producing high-energy fuels. The disclosed method embodiments also concern converting the cyclic diene to a high-energy fuel with improved overall yields that are amenable to industrial scale production. In some embodiments, the high-energy fuel disclosed herein may contain a mixture of one or more cyclic compounds. In one example, the cyclic compounds can be any cyclic compound, such as a fused cyclic compound, which can include one or more bridging points. In one embodiment, the fused cyclic compound can comprise a bridged bicyclic compound having, for example, a 2.2.1 bicyclic configuration.

In some embodiments, the fused cyclic compound can comprise a ring system fused to a bridged ring system, such as endo-tricyclo[5.2.1.0 (2,6)]decane

( ), exo-tricyclo[5.2.1.0 (2,6)] decane ( )

or any combinations thereof. In other embodiments, the fused cyclic compound may be adamantane ( ).

Embodiments of the disclosed method may use one or more steps illustrated below in Scheme 1.

Scheme 1

In some embodiments, carbonyl-containing precursor material 104 can be produced via an acid-catalyzed dehydration reaction of cyclic compounds, such as 5-membered or 6-membered sugars and/or carbohydrates 102, which, in turn, can be obtained by hydrolyzing hemicellulose and/or lignocellulose contained in biomass 100. Biomass 100 may be from any source. Biomass 100 may be derived from a single source, or can comprise a mixture derived from more than one source. In some disclosed embodiments, biomass sources may include, but are not limited to, bioenergy crops, agricultural residues, municipal solid waste, industrial solid waste, sludge from paper manufacturing, yard waste, wood, and forestry waste, or any combinations thereof. In particular disclosed embodiment, biomass may include, but is not limited to, corn grain, corn cobs, crop residues such as corn husks, corn stover, grasses, wheat, wheat straw, barley, barley straw, hay, rice straw, switchgrass, waste paper, sugar cane bagasse, sorghum, soy components obtained from milling of grains, trees, branches, roots, leaves, wood chips, sawdust, shrubs and bushes, vegetables, fruits, flowers, and animal manure, or any combinations thereof.

Lignocellulose from biomass 100 may be used as directly obtained from the biomass source, or may be further processed to increase the availability of lignin, cellulose, hemicellulose, and/or oligosaccharides present in the biomass 100. Biomass 100 may be hydrolyzed in the presence of aqueous acids at temperatures of 100° C. or higher to obtain 5-membered or 6-membered sugars and/or carbohydrates 102. Exemplary acids may include, but are not limited to, mineral acids, such as sulfuric acid, phosphoric acid, hydrochloric acid, or any combinations thereof. In yet additional embodiments, the acids may also be any organic acids, such as oxalic acid, formic acid, acetic acid, an alkyl sulfonic acid, an aryl sulfonic acid, a halogenated acetic acid, a halogenated alkylsulfonic acid, a halogenated aryl sulfonic acid, or any combinations thereof.

In some embodiments, the aqueous acid catalyzes hydrolysis of polysaccharides present in biomass 100 to their corresponding 5-membered or 6-membered monomeric sugars and/or carbohydrates 102. Exemplary polysaccharides of biomass 100 may include, but are not limited to, xylan and glucan, which can be hydrolyzed to corresponding pentoses and/or hexoses 102, which may include, but are not limited to, xylose, arabinose, glucose, galactose, mannose, and the like. Pentoses and/or hexoses 102 are subsequently subjected to a dehydration process to obtain carbonyl-containing precursor compound 104 having a structure satisfying a general formula:

Carbonyl-Containing Precursor Compound 104

With reference to carbonyl-containing precursor compound 104, R and $R^1$ can independently be selected from hydrogen, aliphatic, heteroaliphatic, aromatic, aliphatic-aromatic, heteroaliphatic-aromatic, or any combinations thereof.

In particular disclosed embodiments, R can be selected from hydrogen, alkyl, substituted-alkyl, aryl, heteroaryl (e.g., an oxygen-containing heteroaryl compound), or any combinations thereof; and $R^1$ is H or alkyl (e.g., methyl, ethyl, propyl, butyl, and the like).

In particular disclosed embodiments, carbonyl-containing precursor compound 104 is a furfural, such as when R is and $R^1$ is H.

In another disclosed embodiment, R is —$(CH_2)_n$—$CO_2H$ where n is an integer ranging from 1 to 10 (e.g., 1, 2, 3, 4, 5, 6, 7, 8, 9, or 10), and $R^1$ is alkyl. In particular disclosed embodiments, carbonyl-containing precursor compound 104 is levulinic acid, such as when R is —$(CH_2)_2$—$CO_2H$, and $R^1$ is $CH_3$.

An exemplary embodiment of the dehydration step shown in Scheme 1 can comprise heating pentoses and/or hexoses at a temperature of 130° C. to 200° C., such as 130° C. to 180° C., or 130° C. to 140° C.

As described in Scheme 1, carbonyl-containing precursor compound 104 can subsequently be converted to a corresponding aliphatic alcohol having a structure satisfying a formula Alcohol-Containing Compound 106

With reference to alcohol-containing compound 106, $R^2$ and $R^3$ can join together to provide a ring, such as an aliphatic ring (e.g., a 4-, 5-, 6-, or 7-membered ring). In some embodiments, $R^2$ and $R^3$ can join together to provide a 4-membered aliphatic ring, such as cyclobutanol. In some embodiments, $R^2$ and $R^3$ join together to provide a 5-membered aliphatic ring, such as cyclopentanol. In some embodiments, $R^2$ and $R^3$ join together to provide a 6-membered aliphatic ring, such as cyclohexanol.

In some embodiments, carbonyl-containing precursor compound 104 can be converted to alcohol-containing compound 106 via a single-step selective hydrogenation-rearrangement process in the presence of a catalyst system, such as combination of a metal catalyst and a solid catalyst support. Exemplary catalysts systems can include, but are not limited to, heterogenous metal-based catalyst systems comprising (i) metal selected from copper, cobalt, nickel, iron, ruthenium, palladium, platinum, or a salt thereof, and (ii) a catalyst support, such as activated carbon, a zeolite (e.g., H-ZSM5), or an oxide (e.g., silica-alumina [$SiO_2$—$Al_2O_3$], zirconium oxide [$ZrO_2$], zinc oxide [ZnO], hydrotalcite), or any combinations thereof. A representative method for converting carbonyl-containing precursor compound 104 to alcohol-containing compound 106 is illustrated below in Scheme 2.

Scheme 2

An exemplary embodiment of the above-described method is provided below in Scheme 3.

Scheme 3

In another embodiment, carbonyl-containing precursor compound 104 can be converted to alcohol-containing compound 106 via a two-step conversion method in the presence of a catalyst system, such as a catalyst system comprising a metal catalyst and a solid catalyst support. In the first step, carbonyl-containing precursor compound 104 can undergo a condensation-based rearrangement reaction to produce ketone 106' having a structure satisfying a general formula illustrated below.

Ketone 106'

With reference to ketone 106', $R^2$ and $R^3$ join together to provide a ring, such as a cyclic ketone (e.g., a 4-, 5-, 6-, or 7-membered cyclic ketone). In some embodiments, $R^2$ and $R^3$ join together to provide a 4-membered cyclic ketone, such as cyclobutanone. In some embodiments, $R^2$ and $R^3$ join together to provide a 5-membered cyclic ketone, such as cyclopentanone. In some embodiments, $R^2$ and $R^3$ join together to provide a 6-membered cyclic ketone, such as cyclohexanone.

In some embodiments, the condensation-rearrangement reaction may be accomplished using a catalyst system as disclosed above for alcohol-containing compound 106, but the catalyst system need not be the same for both such conversions. In one example, ketone 106' can be obtained as an aqueous solution, and can be subsequently recovered from water via extraction to obtain pure (or substantially pure) ketone 106'. A representative method for converting carbonyl-containing precursor compound 104 to ketone 106' is illustrated below in Scheme 4.

Scheme 4

An exemplary embodiment of the above-described method is provided below in Scheme 5.

Scheme 5

Ketone 106' can be hydrogenated to corresponding alcohol-containing compound 106 in the presence of a metal catalyst and a solid catalyst support. The metal catalyst and catalyst support used to convert ketone 106' to corresponding alcohol-containing compound 106 can be the same as the metal catalyst and catalyst support as defined above, but it need not be the same catalyst system as used in the other conversions. In yet other embodiments, ketone 106' can be converted to corresponding alcohol-containing compound 106 by using a suitable reducing agent. A person of ordinary skill in the art with the benefit of the present disclosure will understand that any reducing agent capable of reducing a ketone compound to the corresponding alcohol can be used. In an exemplary embodiment, $NaBH_4$ can be used and can provide superior yields as compared to other types of reducing agents. A representative method for converting ketone 106' to alcohol-containing compound 106 using a hydrogenation method is illustrated below in Scheme 6.

Scheme 6

An exemplary embodiment of using a reducing agent is provided below in Scheme 7.

Scheme 7

In yet another embodiment, carbonyl-containing precursor compound 104 can also be converted into a mixture of alcohol-containing compound 106 and ketone 106' by reaction with hydrogen over a solid hydrogenation catalyst system. In some embodiments, the hydrogenation catalyst system can comprise a metal and a support component. Suitable metals can be selected from, but are not limited to, Ni, Co, Cu, Fe, Ru, Pd, Pt, or any combination thereof. Suitable supports can be selected from, but are not limited to $SiO_2$—$Al_2O_3$, $Al_2O_3$, H-ZSM5, activated carbon, $ZrO_2$, ZnO, hydrotalcite, or any combination thereof. This reaction can occur in an aqueous phase with a ratio of water: carbonyl-containing precursor compound 104 ranging from 100:1 to 10:1 by weight, such as 50:1 to 20:1 by weight, or 30:1 to 20:1 by weight. In particular embodiments, a ratio of 20:1 by weight is used. Alcohol-containing compound 106 and ketone 106' can subsequently be separated from the aqueous phase via a liquid-liquid extraction process using solvents, such as ester-containing solvents (e.g., methyl and ethyl esters of fatty acids, high molecular esters like octyl acetate, and/or biodiesel). An additional hydrogenation step can be performed to complete the conversion of ketone 106' to a corresponding alcohol-containing compound 106.

As illustrated in Scheme 1, alcohol-containing compound 106 can be subjected to a catalytic dehydration process to form an alkene-containing compound 108 having a structure satisfying a general formula:

Alkene-Containing Compound 108

With reference to alkene-containing compound 108, $R^2$ and $R^3$ join together to provide a ring, such as an aliphatic ring with the double bond, illustrated above. In particular embodiments, $R^2$ and $R^3$ join together to provide a 5-membered aliphatic ring (such as, cyclopentene).

In some embodiments, alcohol-containing compound 106 can be dehydrated with heating in presence of a dehydrating catalyst at a temperature sufficient to promote dehydration. In some embodiments, the temperature can range from 130° C. to 200° C., such as 150° C. to 200° C., or 190° C. to 200° C. Exemplary dehydrating catalysts may include, but are not limited to, $P_2O_5$, $SiO_2$—$Al_2O_3$, H-mordenite, NAFION® (which is a sulfonated tetrafluoroethylene-based fluoropolymer-copolymer) niobium oxide ($Nb_2O_5$), niobium oxide phosphate ($NbOPO_4$), H-Sulfated-$ZrO_2$, or combinations thereof. A representative method for converting alcohol-containing compound 106 to alkene-containing compound 108 is illustrated below in Scheme 8. With reference to Scheme 8, the dehydrating catalyst can be those mentioned above (and can be H-ZSM5 in some embodiments) and can be combined with alcohol-containing compound 106 and a solvent (e.g., hexadecane) at a suitable temperature (which can be 200° C. in some embodiments using H-ZSM5).

Scheme 8

An exemplary embodiment of the above-described method is provided below in Scheme 9.

Scheme 9

Alkene-containing compound 108 can undergo high temperature pyrolysis to produce a diene-containing compound 110 having a structure satisfying a general formula:

Diene-Containing Compound 110

With reference to diene-containing compound 110, s can be 1 or 2. In some embodiments, when s is 1, diene-containing compound 110 is a 5-membered aliphatic ring (such as, cyclopentadiene). In another embodiment, when s is 2, diene-containing compound 110 is a 6-membered aliphatic ring (such as, cyclohexadiene).

In certain embodiments, alkene-containing compound 108 can be subjected to pyrolysis at a temperature of 500° C. or higher and at a pressure from 1 bar to 10 bar to form diene-containing compound 110. In some embodiments, diene-containing compound 110 may be isolated from the reaction mixture, purified, and subjected to further reaction conditions. A representative method for converting alkene-containing compound 108 to diene-containing compound 110 is illustrated below in Scheme 10.

Scheme 10

An exemplary embodiment of the above-described method is provided below in Scheme 11.

Scheme 11

Additionally, or alternatively, upon prolonged heating, diene-containing compound 110 can undergo dimerization, such as a Diels-Alder dimerization, to form a dimerized compound 112, which is illustrated below.

Dimerized Compound 112

An exemplary embodiment of the dimerization reaction is provided below in Scheme 12.

Scheme 12

Still further, in certain embodiments, diene-containing compound 110 can be converted to form a dehydrated dimerized compound 113 that is partially dehydrated, and having a structure satisfying a general formula as follows wherein s is 1 or 2:

Dehydrated Dimerized Compound 113

In some embodiments, diene-containing compound 110 can react with any remaining unreacted alkene-containing compound 108 at temperatures below 500° C., such as 450° C. to 475° C. or 450° C. to 500° C. to produce partially dehydrated dimerized compound 113. An exemplary embodiment of the partially dehydrated-dimerized reaction is provided below in Scheme 12'.

Scheme 12'

In another embodiment, dimerized compound 112 or partially dehydrated dimerized compound 113 can be permitted to stand at room temperature or can be heated in the range of 60° C. to 100° C. to form a corresponding hydrogenated derivative that serve as a component of high-energy fuel 114. In some embodiments, the hydrogenated cyclic derivative of high-energy fuel 114 can be a cyclic compound, such as the fused cyclic compound discussed above.

In particular disclosed embodiments, dimerized compound 112 can be converted to a corresponding tetrahydro derivative (that is, a compound wherein one or more double bonds of the dimerized compound are converted the corresponding saturated bond). In particular embodiments, cyclopentadiene 312 can be converted to endo-tricyclo[5.2.1.0 (2,6)]decane:

In some embodiments, using prolonged heating, this endo-product can be isomerized to its corresponding exo-product, exo-tricyclo[5.2.1.0 (2,6)]decane:

In some embodiments, the exo-product can be more thermodynamically stable than the endo-product. In some additional embodiments, the exo-product can be converted to adamantane:

In one example, high-energy fuel 114 disclosed herein can be a mixture comprising one or more cyclic compounds, such as exo-tricyclo[5.2.1.0 (2,6)]decane, endo-tricyclo [5.2.1.0 (2,6)]decane, and/or adamantane. In some embodiments comprising all three components, they can be present in the mixture as follows: 96.5% of exo-tetrahydrodicyclopentadiene, 2.5% of endo-tetrahydrodicyclopentadiene, and 1% of adamantane.

Exemplary method embodiments are illustrated below in Schemes 13 and 14.

tion catalyst system, which can comprise a metal catalyst, a catalytic support, or a combination thereof; a second reactor fluidly coupled to the first reactor, the second reactor comprising a second hydrogenation catalyst system; a third reactor fluidly coupled to the second reactor, the third reactor Scheme 13

Scheme 14

High-Energy Fuel
514

VI. System Embodiments for Making High-Energy Fuel

Disclosed herein are system embodiments for making high-energy fuel in a reactor system. In some embodiments, the disclosed system can be used as a "stand-alone" reactor for converting carbonyl-containing precursor compound 104 obtained from biomass 100 to high-energy fuel 114. As used herein, the term "stand-alone" refers to a reactor (or a reactor stage) that is not integrated with another plant, such as a furfural plant, an ethanol plant, or a conventional JP-10 plant. In some embodiments, however, the system can be coupled to or part of such plants. Further, as used herein, the term "reactor stage" refers to a section of a system embodiment described herein that can comprise a reactor that can be coupled to one or more components, such as a feed tank that can supply one or more reactants and/or catalysts, valves, heat exchangers that can control the temperature of the reactor, feed pumps that can control the pressure of the reactor, or any combinations thereof. A person of ordinary skill in the art with the benefit of the present disclosure will understand that system embodiments of the present disclosure can be used to make intermediate products described herein and that reactors used in the system can comprise catalyst systems described herein to convert at least certain intermediate products to other intermediate products and/or final products.

In some embodiments, the system comprises a first reactor comprising a catalyst system, such as a first hydrogenation catalyst system, which can comprise a metal catalyst, a catalytic support, or a combination thereof; a second reactor fluidly coupled to the first reactor, the second reactor comprising a second hydrogenation catalyst system; a third reactor fluidly coupled to the second reactor, the third reactor comprising a dehydrating agent; a furnace fluidly coupled to the third reactor, the furnace comprising a diluent; and a heater component fluidly coupled to the furnace. In some embodiments, the system can further comprise one or more column components configured for separating compounds prepared using the system. In some embodiments, the system can comprise an extraction column, such as a liquid-liquid extraction column; a distillation column; a stripping column; or any combinations thereof. Additional components that can be included in the system include a quench tower, a phase separator component, one or more pumps configured to deliver fluids through flow paths of the system; one or more valves configured to control fluid flow through flow paths of the system; one or more heat exchangers to control/modify temperatures of fluids flowing through flow paths of the system; or any combinations thereof.

Figure 1:
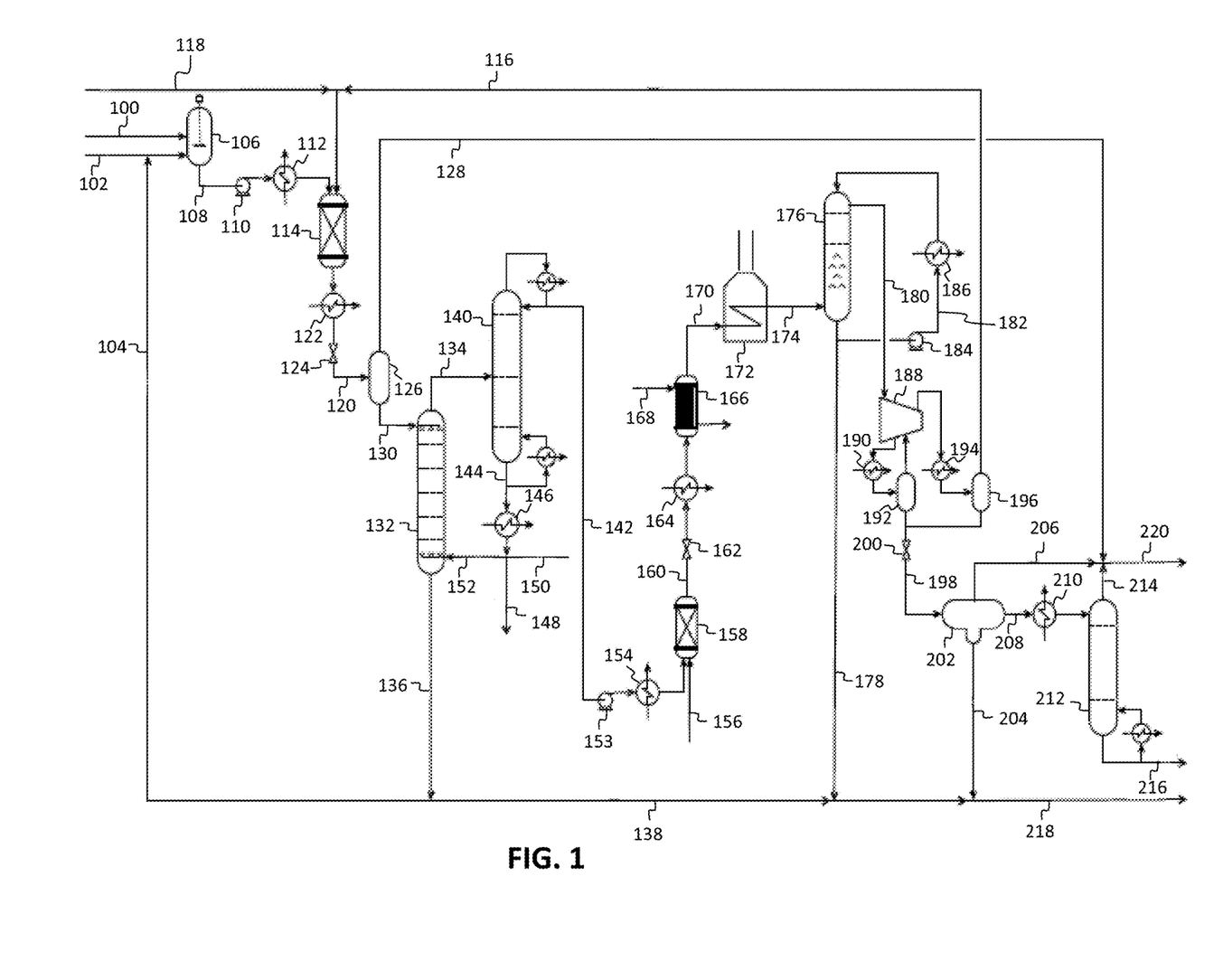
FIG. 1 illustrates a representative process flow diagram of a system embodiment, which shows representative components used for producing a high-energy fuel as described herein.

FIG. 1 is a representative process flow diagram ("PFD") for an exemplary system embodiment for converting carbonyl-containing precursor compound 104 to high-energy fuel 114. The system embodiment illustrated in FIG. 1 can be run in batch mode, or it can be configured for continuous flow operations. In certain disclosed embodiments, the process converts carbonyl-containing precursor compound 104 obtained from a source (e.g., biomass) into dimerized compound 112, which can subsequently be converted to high-energy fuel 114 (e.g., JP-10). The PFD of FIG. 1 also illustrates processing steps and exemplary pumps, valves, heat exchangers, and process vessels used for implementing pressure changes, temperature changes, and/or phase separations used during the method. Additional heat exchanger networks can be implemented to minimize energy consumption. With reference to FIG. 1, exemplary systems can include (but need not include all of) the components referenced below in Table 1.

TABLE 1

Summary of various components of FIG. 1

| Streams | | Equipment | |
| --- | --- | --- | --- |
| Reference Number | Description | Reference Number | Description |
| 100 | Furfural Feed | 132 | Cyclopentanol Extraction Column |
| 102 | Make-up Water | 140 | Cyclopentanol Recovery Column |
| 104 | Recycle Water | 176 | Quench Tower |
| 108 | Aqueous Furfural Solution | 212 | Cyclopentadiene Stripper |
| 118 | High Pressure Hydrogen Feed | 172 | Cyclopentene Dehydrogenation Furnace |
| 116 | Hydrogen Recovered from Process | 112 | Cyclopentanol Reactor Feed Heater |
| 120 | Cyclopentanone/Cyclopentanol Solution | 122 | Cyclopentanol Reactor Product Cooler |
| 130 | Cyclopentanone/Cyclopentanol Solution | 146 | Recycle Solvent Cooler |
| 128 | Gases Removed from Solution | 154 | Hydrogenation Reactor Feed Heater |
| 152 | Solvent | 164 | Cyclopentanol Vaporizer |
| 134 | Extract | 186 | Quench Water Cooler |
| 136 | Raffinate | 190 | Interstage Cooler(s) |
| 138 | Process Water Purge | 194 | Compressor Effluent Cooler |
| 142 | Cyclopentanone/Cyclopentanol Distillate | 210 | Cyclopentadiene Heater/Dimerization |
| 144 | Recovered Solvent | 188 | Multistage Compressor |
| 148 | Solvent Purge | 110 | Cyclopentanol Reactor Feed Pump |
| 150 | Makeup Solvent | 152 | Hydrogenation Reactor Feed Pump |
| 156 | Hydrogen Feed | 184 | Quench Water Recycle Pump |
| 160 | Cyclopentanol | 114 | Cyclopentanol Reactor |
| 168 | Heat Transfer Fluid | 158 | Cyclopentanone Hydrogenation Reactor |
| 170 | Cyclopentene/Water Vapor | 166 | Cyclopentanol Dehydration Reactor |
| 174 | Cyclopentadiene/Hydrogen/Water Vapor | 106 | Cyclopentanol Reactor Feed Tank |
| 178 | Cooled Product Gases | 126 | Degasing Drum |
| 180 | Excess Water from Quench Tower | 192 | Condensate Separation Drum |
| 182 | Recycled Quench Water | 196 | Condensate Separation Drum |
| 198 | Cyclopentadiene/Water Condensates | 202 | Three-Phase Separator |
| 204 | Aqueous Phase Condensate | 124 | Solution Let-down Valve |
| 206 | Dissolved Gases | 162 | Cyclopentanol Let-down Valve |
| 208 | Cyclopentadiene | 200 | Condensate Let-down Valve |
| 218 | Wastewater | | |
| 216 | Dicyclopentadiene Product | | |
| 214 | Gases Removed from Product | | |
| 220 | Fuel Byproduct | | |

Conversion of carbonyl-containing precursor compound 104 to a mixture of alcohol-containing compound 106 and ketone 106'—As discussed above, carbonyl-containing precursor compound 104 can be converted into a mixture of alcohol-containing compound 106 and ketone 106' using hydrogen and a solid hydrogenation catalyst system. Hydrogenation catalyst system used in the conversion of carbonyl-containing precursor compound 104 can be any of the hydrogenation catalyst system described herein. In particular disclosed embodiment, furfural can be converted into a mixture of cyclopentanone and cyclopentanol by reaction with hydrogen over a solid hydrogenation catalyst system. The reaction can occur in the aqueous phase with a water-to-carbonyl-containing precursor compound 104 ratio (such as, water-to-furfural ratio) of 20:1 by weight. In some embodiments, the reaction can occur at temperatures ranging from 140° C. to 200° C. and pressures of 30 to 80 bar.

In particular disclosed embodiments, the process can begin with preparing an aqueous furfural solution. Solely by way of example, in the exemplary embodiment illustrated by FIG. 1, contents from flow path 100 (e.g., furfural), are combined with contents from flow path 102 (e.g., fresh water) and flow path 104 (e.g., recycled water) in tank 106. The pressure of the resulting mixture that passes through flow path 108 is increased to the reaction pressure with pump 110 and the temperature is increased to the desired value using heat exchanger 112 to produce a heated mixture.

The heated mixture is fed to a first reactor, such as reactor 114, which can comprise a hydrogenation catalyst. High-pressure hydrogen from cyclopentene dehydrogenation from flow path 116 (described in more detail herein) is combined with an external source of high-pressure hydrogen introduced via flow path 118 and fed to reactor 114 to complete the conversion of carbonyl-containing precursor compound 104 to a mixture of alcohol-containing compound 106 and ketone 106'. The overall reactions are exothermic; thus, the temperatures emitted from the reaction products exiting from reactor 114 via flow path 120 can be are slightly greater than the inlet temperature.

Separation of alcohol-containing compound 106 and ketone 106' from the aqueous phase—Although conventional distillation processes can be used to separate ketone 106' from water, distillation can be inefficient for recovering a mixture of alcohol-containing compound 106 and ketone 106' from a dilute aqueous solution. Instead, a liquid-liquid extraction process can be used, which can be a more efficient method for separating a mixture of alcohol-containing compound 106 and ketone 106' from the aqueous phase. The solvent selected for the extraction can be a liquid at ambient conditions, can have a low solubility in water and/or a boiling point greater than the mixture of alcohol-containing compound 106 and ketone 106'. Furthermore, water should have a limited solubility in the solvent. In some embodiments, high molecular weight esters can be utilized as solvents for the extraction process, and such high molecular weight esters may include, but are not limited to, octyl acetate and methyl and ethyl esters of fatty acids (or other solvents described herein). Additionally, or alternatively, mixtures of high molecular weight esters, such as biodiesel, also may be good solvents for the extraction of the mixture from the aqueous phase.

In some embodiments, the liquid-liquid extraction can take place at near ambient conditions (such as, 20° C. to 50° C.), so the reaction products in flow path 120 can be cooled and depressurized before being fed to the extraction process. The reaction products are first cooled to near ambient temperature in heat exchanger 122. The mixture is reduced to atmospheric pressure through valve 124. Contents in flow path 120 are then fed to degassing drum 126 where any dissolved gases released during depressurization (such as through flow path 128) are separated from the liquid (which flows through flow path 130). The aqueous solution containing the mixture of alcohol-containing compound 106 and ketone 106' is fed via flow path 130 to the top of extraction column 132, which is configured to utilize a counter-current liquid-liquid extraction process. The solvent at near ambient temperature is fed to the bottom of extraction column 132. The extract exits extraction column 132 at the top via flow path 134, which can contain the solvent containing the cyclopentanone and cyclopentanol. The raffinate exits at the bottom of extraction column 132 via flow path 136, which includes the water with the cyclopentanone and cyclopentanol removed. A portion of the raffinate is purged from the process via flow path 138 to prevent the accumulation of by-products and contaminants. The remaining portion is recycled to tank 106 via flow path 104.

The extract is fed to a distillation column, such as recovery column 140, via flow path 134. Recovery column 140 can be a distillation column that separates the mixture comprising alcohol-containing compound 106 and ketone 106' from the solvent. The mixture of alcohol-containing compound 106 and ketone 106' typically can have higher boiling points from the solvent, and therefore the mixture can be concentrated in the distillate via flow path 142. The bottom product of the column contains the recovered solvent and is emitted via flow path 144.

Because extraction column 132 operates at ambient pressure, the recovered solvent in flow path 144 can be cooled to prevent boiling in the column. This cooling can be accomplished using heat exchanger 146. A portion of the recovered solvent can be purged via flow path 148 to prevent the accumulation of by-products and contaminants. The purge combined with solvent that is dissolved in the raffinate may result in a net loss of solvent. Therefore, makeup solvent may be used which can be supplied via flow path 150. The makeup solvent is combined with the portion of the contents of flow path 144 that has not been purged and fed to extraction column 132 via flow path 152.

Hydrogenation of ketone 106' to alcohol-containing compound 106—The reduction reaction that occurs in reactor 114 produces a mixture of alcohol-containing compound 106 and ketone 106'. Therefore, in some embodiments, an additional hydrogenation reaction may be performed to complete the conversion of ketone 106' to alcohol-containing compound 106. For example, hydrogenation of ketone 106' can be accomplished with an exothermic liquid-phase reaction catalyzed by a solid hydrogenation catalyst system. The hydrogenation catalyst systems utilized in hydrogenation of ketone 106' can be any of the hydrogenation catalyst systems defined herein. In some embodiments, the reaction can occur at 200° C. Since maintaining the mixture of alcohol-containing compound 106 and ketone 106' in the liquid phase and promoting mass transfer of hydrogen gas into the liquid phase may be performed at high pressure, the system may be maintained at a pressure of 20 bar.

The mixture of alcohol-containing compound 106 and ketone 106', which flows through flow path 142 from recovery column 140, can be maintained at ambient pressure and a temperature between 130° C. and 140° C. Pump 152 increases the pressure of contents flowing through flow path 142 to the reaction pressure and heat exchanger 154 increases temperature to the reaction temperature. The alcohol-containing compound 106/ketone 106' mixture and hydrogen gas included in flow path 156 are fed to hydrogenation reactor 158 where any ketone 106' present in the feed is completely converted to alcohol-containing compound 106. The reactor product contained in flow path 160 comprises alcohol-containing compound 106 and can further comprise trace amounts of dissolved hydrogen and other contaminants.

Dehydration of alcohol-containing compound 106 to alkene-containing compound 108-Dehydration of alcohol-containing compound 106 to alkene-containing compound 108 is an endothermic gas-phase catalytic reaction. Because the number of moles increases in this endothermic gas-phase reaction, low operating pressure favors this reaction. In some embodiments, complete conversion to alkene-containing compound 108 can be achieved at 200° C. and 1 bar pressure.

Hydrogenation reactor 158 produces pressurized alcohol-containing compound 106, which flows through flow path 160. To achieve the suitable feed conditions for the dehydration reaction, pressurized alcohol-containing compound 106 can be depressurized through valve 162. Depressurization vaporizes a portion of alcohol-containing compound 106. Heat exchanger 164 completes the vaporization and superheats alcohol-containing compound 106 to the reaction temperature. Alcohol-containing compound 106 is then fed to dehydration reactor 166. This unit operation is a tubular reactor comprising the solid dehydrating catalyst. Dehydrating catalyst employed in the dehydration of alcohol-containing compound 106 to alkene-containing compound 108 can be any of the dehydrating catalysts described above. Steam or other heat transfer fluid from flow path 168 supplies heat for this endothermic reaction. The product of the reaction is an equimolar mixture of alkene-containing compound 108 and steam.

Dehydrogenation of alkene-containing compound 108 to diene-containing compound 110—Alkene-containing compound 108 can undergo high-temperature pyrolysis to produce a diene-containing compound 110. For example, cyclopentene undergoes high temperature pyrolysis to produce dicyclopentadiene. Because the number of moles increases in this endothermic gas-phase reaction, equilibrium favors high reaction temperatures and low reaction pressures. In some embodiments, nearly 100% conversion can be achieved at a pressure within a range from 1 bar to 10 bar, and a temperature within a range 450° C. to 600° C. In particular disclosed embodiments, nearly 100% conversion can be achieved at a pressure of 1 bar and a temperature of 600° C. The primary by-products may include, but are not limited to, ethylene and propylene. Thermodynamics also favor coke formation.

The product produced by dehydration reactor 166 can contain equimolar quantities of alkene-containing compound 108 and steam from flow path 170. The steam is not separated from alkene-containing compound 108 because it can be beneficial in dehydrogenation furnace 172. For example, the steam reduces the partial pressure of alkene-containing compound 108, which favors eventual conversion to diene-containing compound 110. Steam also inhibits coke formation and reacts with any coke that might form to produce hydrogen and carbon monoxide. In some embodiments, a diluent, such as an inert diluent can be introduced into the furnace. Suitable diluents can include, but are not limited to, fused silica, SiC, quartz beads, silica sand, silicon dioxide, or any combinations thereof.

Recovery of diene-containing compound 110—In some embodiments, the product from dehydrogenation furnace 172 is a gas mixture comprising diene-containing compound 110, hydrogen, and steam with small amounts of ethylene and propylene contained in flow path 170. To produce dimerized compound 112, contents from flow path 174 can be cooled and the major components separated. This separation can be accomplished in a three-step process as described below.

First, contents from flow path 174 are fed to quench tower 176 where the gas is cooled by direct contact with water. The cooling condenses a significant portion of the steam resulting a cooler gas stream that flows via flow path 180 and comprises diene-containing compound 110, hydrogen, and less than 10 mole % water vapor. The quench water exits quench tower 176 at the bottom, excess water is purged (via flow path 178), and the remaining water is recirculated with the pump 184 via flow path 182. The recycled quench water is cooled in a heat exchanger 186 before it is fed back to quench tower 176. The cooled gas (contained in flow path 180) is compressed in compressor 188 to 80 bar. Compressor 188 is a multi-staged device with inter-stage cooling. At each stage, one or more interstage coolers (e.g., cooler 190) condense some of the diene-containing compound 110 and water, which is separated from the gas in drum 192. The compressor effluent is cooled in compressor cooler 194, and the condensate is separated from the high-pressure hydrogen gas (included in flow path 116) in condensate drum 196.

The condensate from each stage of the compression is combined in flow path 198 and depressurized to ambient pressure through valve 200. This stream typically comprises an organic phase comprising diene-containing compound 110; an aqueous phase; and a gas phase comprising hydrogen, ethylene, and propylene. Contents from flow path 198 are fed to three-phase separator 202, which comprises three product streams—an aqueous stream (in flow path 204), a gas stream (in flow path 206), and the organic phase comprising diene-containing compound 110 (in flow path 208).

Production and purification of dimerized compound 112—diene-containing compound 110 can be converted to dimerized compound 112 when the reaction mixture is heated to a sufficient temperature. In some embodiments, the temperature can be within a range from 25° C. to 100° C. In particular disclosed embodiment, endo-dicyclopentadiene can form when the reaction mixture is heated at 100° C. Because the reaction is very rapid, diene-containing compound 110 only needs to be heated at 100° C. A separated dimerization reactor may not be needed. In some embodiments, and as described above, dehydrated dimerized compound 113 may also be obtained from diene-containing compound 110, either along with dimerized compound 112 or alone, which can also be converted to corresponding hydrogenated derivative that constitutes cyclic compound of high-energy fuel 114 as described herein.

Diene-containing compound 110 (present in flow path 208) from three-phase separator 202 is fed to the heater 210 where it can be heated to 100° C. and dimerized to dimerized compound 112 (e.g., endo-dicyclopentadiene). The product of this reactor is fed to stripper 212 to remove dissolved gases and low boiling contaminants. The dissolved gases and low boiling contaminants exit the column overhead as a gas stream via flow path 214. The bottom product is dimerized compound 112 (in flow path 216), which is pure.

Waste Streams—The process water purge in flow path 138 from extraction column 132, excess water in flow path 180 from quench tower 176, and aqueous phase condensate in flow path 204 from three-phase separator 202 can be combined into single wastewater flow path 218, which comprises organic contaminants. This waste stream can be treated to remove the contaminants before it can be reused in the process or discharged into the environment.

Contents in flow path 128 from the degassing drum 126, contents from flow path 206 from three-phase separator 202, and contents from flow path 214 from stripper 212 are gas streams rich in hydrogen and organic vapors. These three streams can be combined into a single fuel stream in flow path 220, which can be used along with natural gas as fuel for the process.

V. Overview of Several Embodiments

Disclosed herein are embodiments of a system, comprising: a first reactor comprising first hydrogenation catalyst system; a second reactor fluidly coupled to the first reactor, the second reactor comprising a second hydrogenation catalyst system; a third reactor fluidly coupled to the second reactor, the third reactor comprising a dehydrating agent; a furnace fluidly coupled to the third reactor, the furnace comprising a diluent; and a heater component fluidly coupled to the furnace.

In some embodiments, the first and second hydrogenation catalyst independently comprise a metal catalyst and a catalytic support.

In any or all of the above embodiments, the metal catalyst is a metal selected from copper, cobalt, nickel, iron, ruthenium, palladium, platinum or a salt thereof; and the catalytic support is an activated carbon, a zeolite, an oxide, or any combinations thereof.

In any or all of the above embodiments, the catalytic support is selected from $Al_2O_3$, H-ZSM5, activated C, $ZrO_2$, ZnO, hydrotalcite, or any combination thereof.

In any or all of the above embodiments, the dehydrating agent is selected from $P_2O_5$, $SiO_2$—$Al_2O_3$, H-mordenite, a sulfonated tetrafluoroethylene-based fluoropolymer-copolymer, niobium oxide, niobium oxide phosphate, H-Sulfated-$ZrO_2$, or any combinations thereof.

In any or all of the above embodiments, the first reactor and the second reactor are fluidly coupled to a $H_2$ source.

In any or all of the above embodiments, the furnace further comprises steam.

In any or all of the above embodiments, the system further comprises an extraction column fluidly coupled to the first reactor, wherein the extraction column is positioned between the first reactor and the second reactor.

In any or all of the above embodiments, the system further comprises a distillation column fluidly coupled to the extraction column, wherein the distillation column is positioned between the extraction column and the second reactor.

In any or all of the above embodiments, the system further comprises a quench tower fluidly coupled to the furnace, wherein the quench tower comprises water.

In any or all of the above embodiments, the system further comprises a pump, a heat exchanger, or a combination thereof, wherein the pump, the heat exchanger, or both are fluidly coupled to the quench tower.

In any or all of the above embodiments, the system further comprises a phase separator component fluidly coupled to the quench tower, wherein the phase separator component separates any gases, aqueous liquids, and/or organic liquids present in a feed introduced into the phase separator.

In any or all of the above embodiments, the system further comprises a stripping column fluidly coupled to the heater.

Also disclosed herein are embodiments of a system comprising: a feed tank; a first reactor comprising a first hydrogenation catalyst system, wherein the first reactor is fluidly coupled to the feed tank; an extraction column fluidly coupled to the first reactor; a distillation column fluidly coupled to the extraction column; a second reactor comprising a second hydrogenation catalyst system, wherein the second reactor is fluidly coupled to the distillation column; a third reactor comprising a dehydrating agent, wherein the third reactor is fluidly coupled to the second reactor; a furnace comprising an inert diluent, wherein the furnace is fluidly coupled to the third reactor; a quench tower fluidly coupled to the furnace; a phase separator component coupled to the furnace; a heater fluidly coupled to the phase separator component; a stripper column fluidly coupled to the heater; and wherein the system is configured as a continuous flow system.

In some embodiments, the system further comprises one or more pumps to facilitate fluid flow through the system; one or more valves to control fluid flow through the system; one or more heat exchangers to modify temperatures of fluids passing through the system; or any combinations thereof.

Also disclosed herein are embodiments of a process, comprising: hydrogenating a carbonyl-containing precursor with a catalyst system to produce a mixture comprising an alcohol-containing compound; treating the mixture with hydrogen gas to produce a pressurized alcohol-containing compound; and converting the pressurized alcohol-containing compound to at least one fused cyclic compound suitable for use as a high-energy fuel.

In some embodiments, the carbonyl-containing precursor is derived from biomass.

In any or all of the above embodiments, the carbonyl-containing precursor compound is furfural.

In any or all of the above embodiments, the catalyst system comprises (i) a metal selected from Co, Cu, Fe, Ru, Pd, Pt, or any combination thereof; and (ii) a support selected from an activated carbon, a zeolite, an oxide, or any combinations thereof.

In any or all of the above embodiments, the mixture further comprises a ketone, and treating the mixture comprises treating the mixture with hydrogen gas to completely hydrogenate the ketone and the alcohol-containing compound to produce the pressurized alcohol-containing compound.

In any or all of the above embodiments, converting the pressurized alcohol-containing compound comprises dehydrating the pressurized alcohol-containing compound with a dehydrating agent to produce an alkene-containing compound and then pyrolyzing the alkene-containing compound to a diene-containing compound.

In any or all of the above embodiments, the process further comprises dimerizing the diene-containing compound to provide the at least one fused cyclic compound suitable for use as a high-energy fuel.

Also disclosed herein are embodiments of a system comprising: a first reactor stage that comprises a first reactor housing a catalyst on a catalytic support, wherein the first reactor stage is configured to hydrogenate a carbonyl-containing precursor compound to provide a mixture comprising an alcohol-containing compound; a second reactor stage comprising a second reactor, wherein the second reactor stage is fluidly coupled to the first reactor stage and is configured to convert the mixture to a pressurized alcohol-containing compound; and a third reactor stage comprising a third reactor that houses a dehydrating agent, wherein the third reactor stage is fluidly coupled to the second reactor stage and is configured to convert the pressurized alcohol-containing compound to at least one fused cyclic compound that is suitable for use as a high-energy fuel.

In any or all of the above embodiments, the first reactor stage is configured to expose the catalyst in the first reactor to pressurized recycled hydrogen gas and an external source of pressurized hydrogen gas to thereby hydrogenate the carbonyl-containing precursor compound.

In any or all of the above embodiments, the first reactor stage is configured to maintain the carbonyl-containing precursor compound at a first temperature.

In any or all of the above embodiments, the first reactor stage is further configured to hold the mixture at a second temperature that is greater than the first temperature of the carbonyl-containing precursor compound.

In any or all of the above embodiments, the first reactor stage comprises a first extraction column that is fluidly coupled to the first reactor stage, wherein the first extraction column is configured to extract the mixture of the first reactor stage from an aqueous phase.

In any or all of the above embodiments, the mixture further comprises a ketone, and the second reactor of the second reactor stage comprises hydrogen gas and is fluidly coupled to a second extraction column, wherein the second reactor stage is configured to completely convert the mixture to the alcohol-containing compound. In some embodiments, the dehydrating agent converts the pressurized alcohol-containing compound to an alkene-containing compound.

In any or all of the above embodiments, the system comprises a third reactor stage that is configured to pyrolyze the alkene-containing compound to a diene-containing compound.

In any or all of the above embodiments, the third reactor stage is further configured to dimerize the diene-containing compound to the at least one fused cyclic compound suitable for use as a high-energy fuel.

VI. Examples

Example 1

Figure 2:
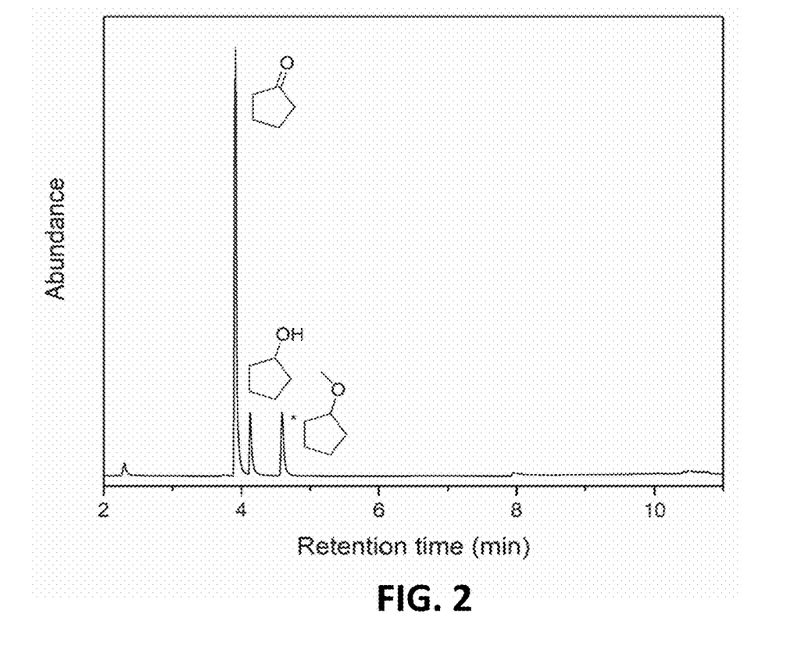
FIG. 2 is a representative GC-MS spectrum of cyclic intermediate products obtained using a method embodiment disclosed herein.

Representative example for hydrogenation of furfural (Compound 304) to cyclopentanol (compound 306)/cyclopentanone (Compound 306'): A stainless steel pressure tube containing a magnetic stir bar was charged with $CuO/Al_2O_3$ (0.101 g, 13 wt. % Cu, 0.207 mmol Cu), $H_2O$ (4.000 g, 221.975 mmol), and $H_2$ (24 bar). The apparatus was heated to 200° C. with stirring (500 rpm) for 2 hours. The apparatus was then cooled by submerging in a cold-water bath. The cold-water bath was allowed to cool for 15 minutes. At this point, the apparatus was vented and furfural (0.304 g, 3.164 mmol), $H_2O$ (4.000 g, 221.975 mmol), and $H_2$ (at a pressure of 24 bar) were added. The apparatus was again heated to 200° C. with stirring (at 500 rpm) for 3 hours. The apparatus was then cooled by submerging in a cold-water bath. The cold-water bath was allowed to cool for 15 minutes. At this point, the reaction of furfural was complete. The pressure was relieved, the reaction mixture was transferred to a centrifuge tube, and methanol (1.0 mL) was used to rinse the pressure tube. Upon centrifugation, the combined supernatant was decanted from the catalysts and diluted with methanol in a volumetric flask (10.0 mL). The sample was then analyzed by GC/MS and yields were determined using calibration curves generated from authentic standards of the products, cyclopentanone and cyclopentanol. An exemplary GC/MS trace of aqueous furfural products is provided by FIG. 2. Yields using different catalyst systems are provided in Table 2, below.

TABLE 2

| Catalyst | % Yield Cyclopentanone | % Yield Cyclopentanol |
|---|---|---|
| $CuO/Al_2O_3$ | 72.9 | 1.3 |
| Cu/C | 66.6 | 1.0 |
| Ni/C | 38.2 | 10.6 |
| Ni—Ru/C | 29.5 | 34.4 |
| $Ru/Al_2O_3$ | 23.2 | 30.3 |
| Ru/C | 19.8 | 37.6 |

Example 2

Representative example for hydrogenation of cyclopentanone (compound 306') to cyclopentanol (compound 306): A stainless steel pressure tube containing a magnetic stir bar was charged with $Ni/SiO_2$—$Al_2O_3$(0.100 g, 62 wt. % Ni, 1.056 mmol Ni), cyclohexane (7.0 mL), cyclopentanone (0.504 g, 5.991 mmol) and $H_2$ (at a pressure of 14 bar). The apparatus was heated to 120° C. with stirring (500 rpm) for 2 hours. The apparatus was then cooled by submerging in a cold-water bath. The cold-water bath was allowed to cool for 15 minutes. The pressure was relieved, the reaction mixture was transferred to a centrifuge tube, and methanol (1.0 mL) was used to rinse the pressure tube. Upon centrifugation, the combined supernatant was decanted from the catalysts and diluted with methanol in a volumetric flask (10.0 mL). The sample was then analyzed by GC/MS and a quantitative yield was determined using calibration curves generated from authentic standards of cyclopentanone and cyclopentanol.

Example 3

Figure 3:
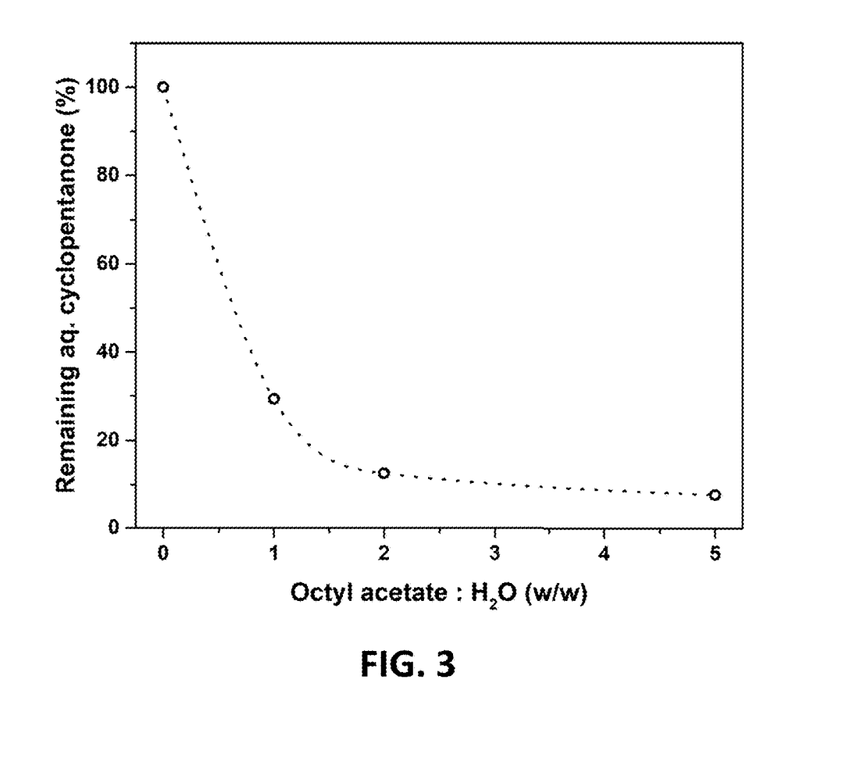
FIG. 3 is a graph showing cyclopentanone recovery from water at varying ratios of octyl acetate to water.

Recovery of cyclopentanone (compound 306') from water:Aqueous cyclopentanone (compound 306') solutions (0.45 M) containing internal standard (4,4-dimethyl-4-silapentane-1-sulfonic acid, 0.0092 M) were extracted with varying ratios of water:octyl acetate (1:1, 1:2, 1:5 w/w). The solutions were stirred for 5 minutes at ambient temperature and then the aqueous phase was analyzed by $^1H$ NMR spectroscopy to determine the remaining cyclopentanone using the internal standard. At a water:octyl acetate ratio of 1:5, 7.6% of the cyclopentanone remained in the aqueous phase. FIG. 3 shows an exemplary graph illustrating recovery of cyclopentanone from water at varying octyl acetate:water ratios.

Example 4

Figure 4:
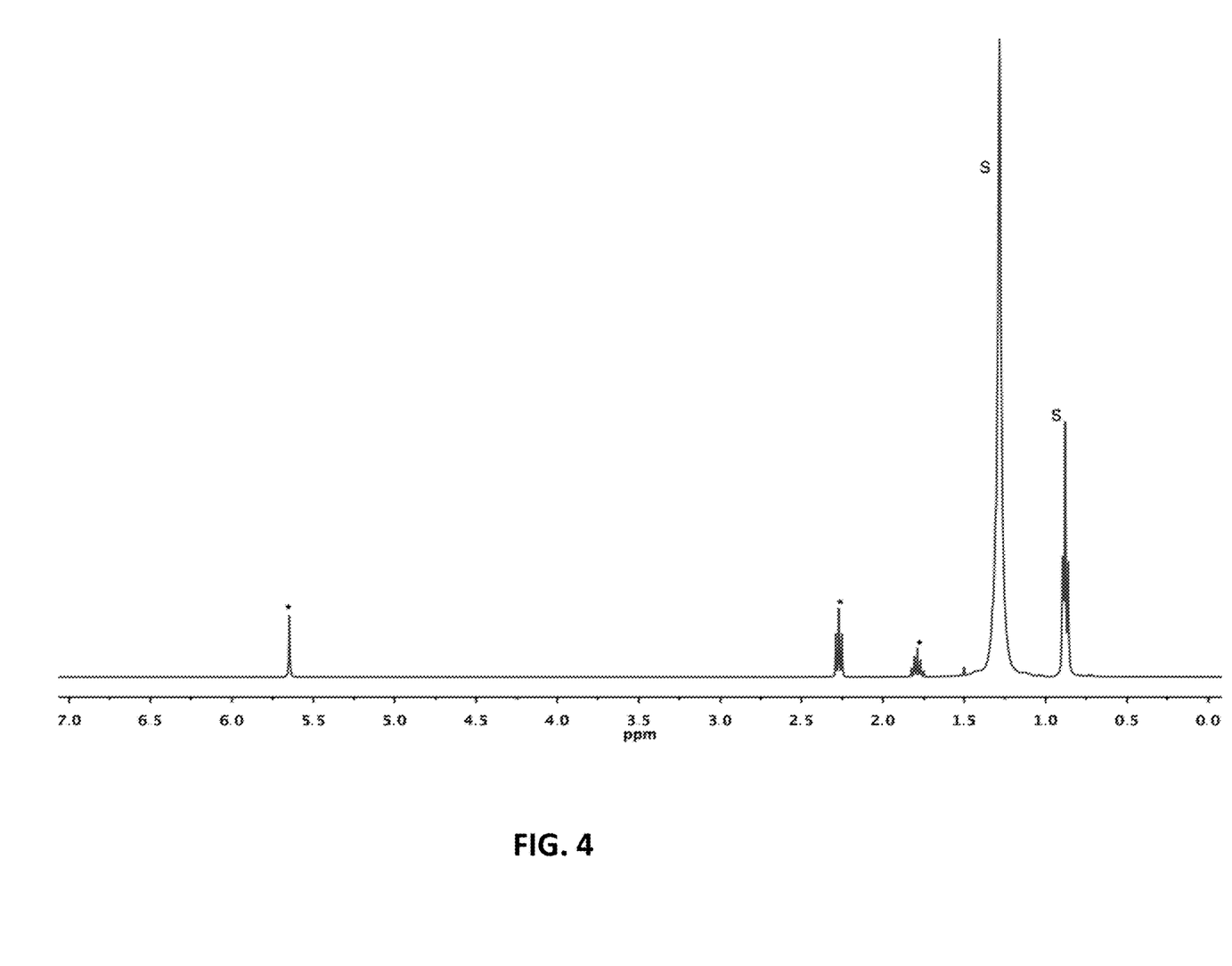
FIG. 4 is a representative $^1$H-NMR spectrum of a reaction mixture from cyclopentanol in hexadecane solvent.

Representative example for dehydration of cyclopentanol (compound 306) to cyclopentene (compound 308): Cyclopentanol (0.500 mL; 5.509 mmol) and hexadecane (4.5 mL) were charged into a glass vial containing H-ZSM5 (0.296 g) and a stirbar. The vial was sealed and placed in a pre-heated aluminum block at 200° C. with stirring (500 rpm) for 5 minutes. After that time, the reaction was then cooled by submerging in a cold-water bath. The cold-water bath was allowed to cool for 15 minutes. Removal of the catalyst by filtration and analysis by $^1H$ and $^{13}C$ NMR spectroscopy revealed quantitative conversion to cyclopentene. FIG. 4 shows a representative $^1H$ NMR spectrum of a reaction mixture from cyclopentanol and H-ZSM5 in hexadecane.

Example 5

Figure 5:
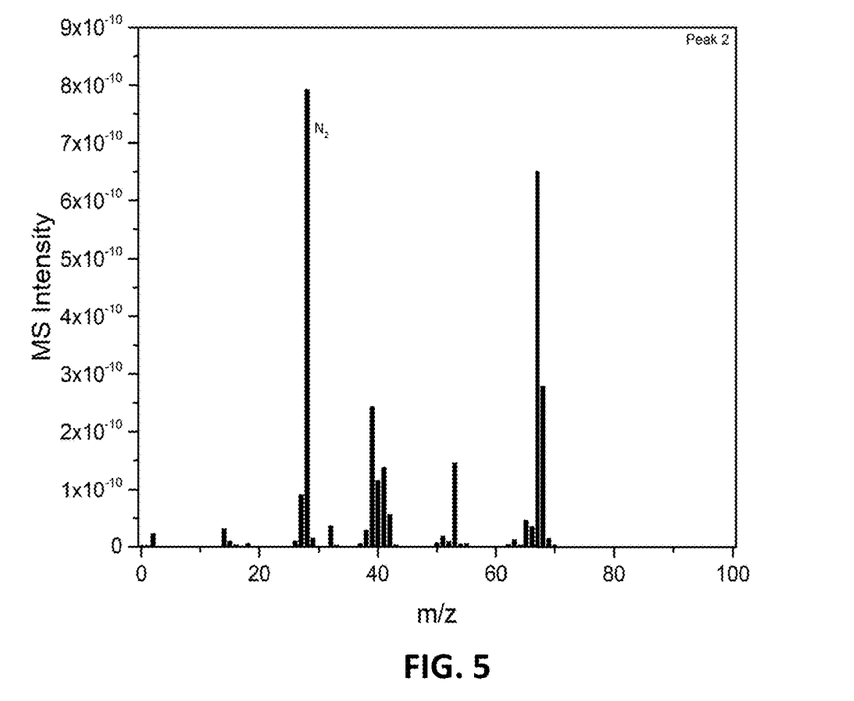
FIG. 5 is a mass spectrum of vapors entering a furnace component of a system embodiment, which indicates the presence of cyclopentene (m/z=68).
Figure 6:
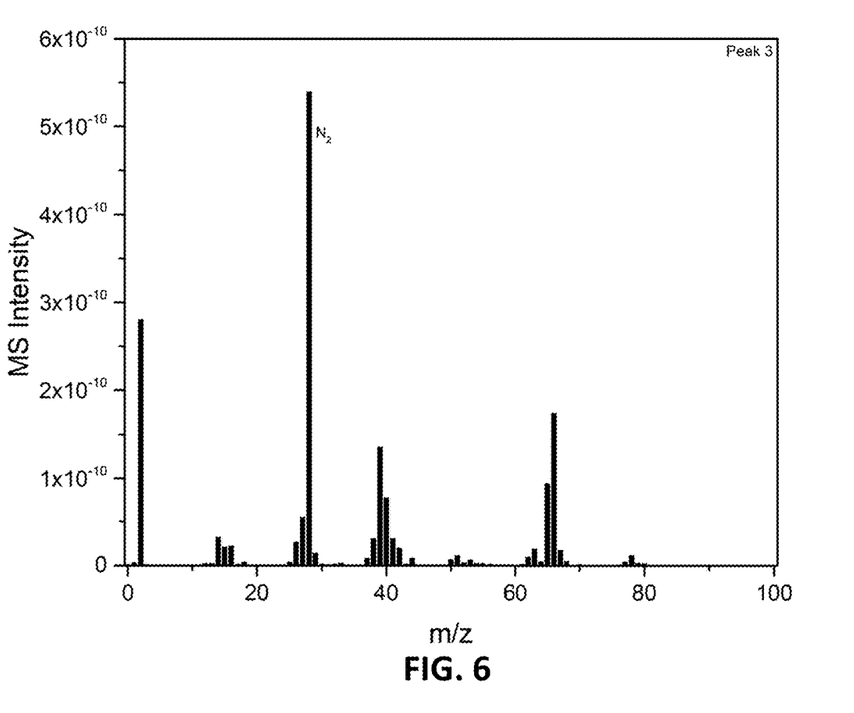
FIG. 6 is a mass spectrum of vapors exiting a furnace component of a system embodiment, which indicates the presence of cyclopentadiene (m/z=66).

Representative example of cyclopentene pyrolysis to cyclopentadiene and hydrogen: Cyclopentene vapors (5 mL, atmospheric pressure) were injected into a nitrogen flow (20 mL/min, atmospheric pressure) and passed over a bed of inert SiC diluent (2") in a quartz U-tube (¼" OD, ⅛" ID, 8" total length) inside a furnace at 690° C. The exiting vapors were sampled using a residual gas analyzer by mass spectrometry and determined to be hydrogen and cyclopentadiene. FIG. 5 shows a mass spectrum of entering cyclopentene vapors, where the m/z=68 peak represents cyclopentene. FIG. 6 shows a mass spectrum of exiting reactor vapors, where the m/z=66 and m/z=2 peaks represent cyclopentadiene and hydrogen, respectively.

In view of the many possible embodiments to which the principles of the present disclosure may be applied, it should be recognized that the illustrated embodiments are only preferred examples, and should not be taken as limiting. Rather, the scope of the present disclosure is defined by the following claims. We therefore claim as our invention all that comes within the scope and spirit of these claims.

We claim:

1. A method, comprising:

hydrogenating a carbonyl-containing precursor compound having a Formula I with a catalyst system and hydrogen gas to produce a mixture comprising an alcohol-containing compound having a Formula II; and converting the alcohol-containing compound to a diene-containing compound by dehydrating the alcohol-containing compound with a dehydrating agent to produce an alkene-containing compound and then pyrolyzing the alkene-containing compound to a diene-containing compound; wherein Formula I is wherein R is an oxygen-containing heteroaryl compound and $R^1$ is hydrogen or alkyl; and Formula II is wherein $R^2$ and $R^3$ join together to provide an aliphatic ring.

2. The method of claim 1, wherein the carbonyl-containing precursor compound is derived from biomass.

3. The method of claim 1, wherein the carbonyl-containing precursor compound is furfural.

4. The method of claim 1, wherein the catalyst system comprises (i) a metal selected from Ni, Co, Cu, Fe, Ru, Pd, Pt, or any combination thereof; and (ii) a catalytic support selected from an activated carbon, a zeolite, an oxide, or any combinations thereof.

5. The method of claim 1, wherein the mixture comprising the alcohol-containing compound further comprises a ketone, and the method further comprises hydrogenating the ketone to produce a further amount of the alcohol-containing compound.

6. The method of claim 1, further comprising dimerizing the diene-containing compound to provide at least one fused cyclic compound comprising a bridged bicyclic skeleton.

7. A method, comprising;
hydrogenating a carbonyl-containing precursor compound having a Formula I with a catalyst system and hydrogen gas to produce a mixture comprising an alcohol-containing compound having a Formula II; and
converting the alcohol-containing compound to at least one fused cyclic compound comprising a bridged bicyclic skeleton by (i) dehydrating the alcohol-containing compound with a dehydrating agent to produce an alkene-containing compound and then pyrolyzing the alkene-containing compound to a diene-containing compound; and (ii) dimerizing the diene-containing compound to provide the at least one fused cyclic compound; wherein Formula I is wherein R is an oxygen-containing heteroaryl compound and $R^1$ is hydrogen or alkyl; and Formula II is wherein $R^2$ and $R^3$ join together to provide an aliphatic ring.

8. The method of claim 7, wherein the carbonyl-containing precursor compound is derived from biomass.

9. The method of claim 7, wherein the carbonyl-containing precursor compound is furfural.

10. The method of claim 7, wherein the catalyst system comprises (i) a metal selected from Ni, Co, Cu, Fe, Ru, Pd, Pt, or any combination thereof; and (ii) a catalytic support selected from an activated carbon, a zeolite, an oxide, or any combinations thereof.

11. The method of claim 7, wherein the mixture comprising the alcohol-containing compound further comprises a ketone, and the method further comprises hydrogenating the ketone to produce a further amount of the alcohol-containing compound.

* * * * *